(12) United States Patent
Ichihashi

(10) Patent No.: US 12,257,452 B2
(45) Date of Patent: Mar. 25, 2025

(54) RADIOTHERAPY PLANNING APPARATUS AND METHOD

(71) Applicant: Canon Medical Systems Corporation, Otawara (JP)

(72) Inventor: Masahide Ichihashi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 297 days.

(21) Appl. No.: 17/821,842

(22) Filed: Aug. 24, 2022

(65) Prior Publication Data

US 2023/0063685 A1 Mar. 2, 2023

(30) Foreign Application Priority Data

Aug. 25, 2021 (JP) ................. 2021-136953
Aug. 22, 2022 (JP) ................. 2022-132053

(51) Int. Cl.
*A61N 5/10* (2006.01)

(52) U.S. Cl.
CPC ........... *A61N 5/103* (2013.01); *A61N 5/1065* (2013.01)

(58) Field of Classification Search
CPC .............................. A61N 5/103; A61N 5/1065
See application file for complete search history.

(56) References Cited

U.S. PATENT DOCUMENTS

| | | | |
|---|---|---|---|
| 5,418,827 A * | 5/1995 | Deasy | A61N 5/103 378/65 |
| 10,507,337 B2 | 12/2019 | Willcut et al. | |
| 2020/0286601 A1 | 9/2020 | Khuntia et al. | |

FOREIGN PATENT DOCUMENTS

JP 2020-533123 A 11/2020

OTHER PUBLICATIONS

Extended European Search Report issued Jan. 19, 2023 in European Patent Application No. 22191968.1, 6 pages.

* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, a radiotherapy planning apparatus includes processing circuitry. The processing circuitry is configured to acquire dose rate distribution information indicating distribution of a dose rate in an irradiation path of radiation based on irradiation conditions of the radiation. The processing circuitry is configured to acquire irradiation effect discrimination information for discriminating irradiation effects of radiation in the irradiation path based on the acquired dose rate distribution information.

11 Claims, 9 Drawing Sheets

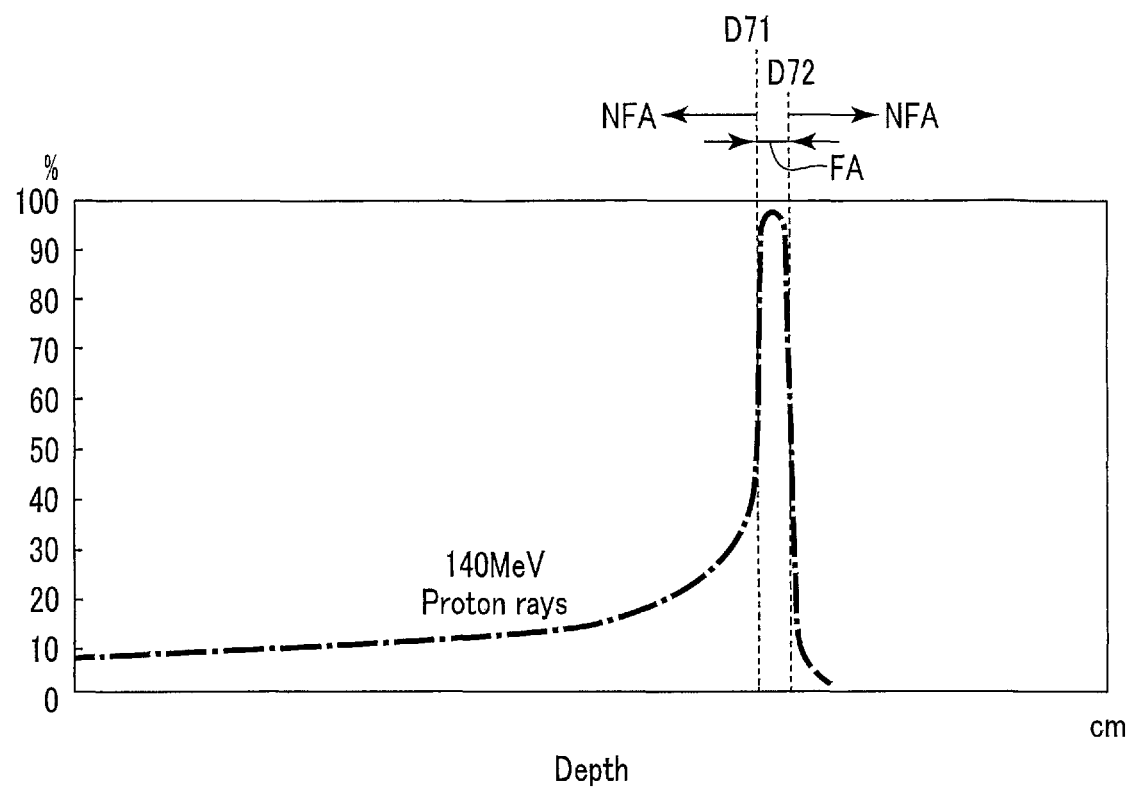
F I G. 11

RADIOTHERAPY PLANNING APPARATUS AND METHOD

CROSS-REFERENCE TO RELATED APPLICATIONS

This application is based upon and claims the benefit of priority from the prior Japanese Patent Applications No. 2021-136953, filed Aug. 25, 2021, and No. 2022-132053, filed Aug. 22, 2022, the entire contents of all of which are incorporated herein by reference.

FIELD

Embodiments described herein relate generally to a radiotherapy planning apparatus and method.

BACKGROUND

A high dose-rate radiation in which radiation is applied at an extremely high dose rate (for example, 40 Gy/sec) compared to a conventional dose rate (for example, 0.03 Gy/sec) in a short time (called "FLASH radiotherapy") is known in the field of radiotherapy. With FLASH radiotherapy, a targeted tumor can be treated with minimum damage to healthy tissue (hereinafter, "FLASH irradiation effect"); therefore, FLASH radiotherapy is expected to minimize side effects and achieve safer radiotherapy compared to conventional radiotherapy.

Since radiation of electron beams (MeV) or the like attenuates according to a depth in an irradiated body, if a high dose rate needed to attain the FLASH irradiation effect cannot be maintained throughout a FLASH irradiation path, electron beam irradiation may damage healthy tissue.

BRIEF DESCRIPTION OF THE DRAWINGS

FIG. 11 is a diagram showing a depth at which a FLASH area and a non-FLASH area are separated by the Bragg peak of proton rays shown in FIG. 9.

DETAILED DESCRIPTION

In general, according to one embodiment, a radiotherapy planning apparatus includes processing circuitry. The processing circuitry is configured to acquire dose rate distribution information indicating distribution of a dose rate in an irradiation path of radiation based on irradiation conditions of the radiation. The processing circuitry is configured to acquire irradiation effect discrimination information for discriminating irradiation effects of radiation in the irradiation path based on the acquired dose rate distribution information.

Figure 1:
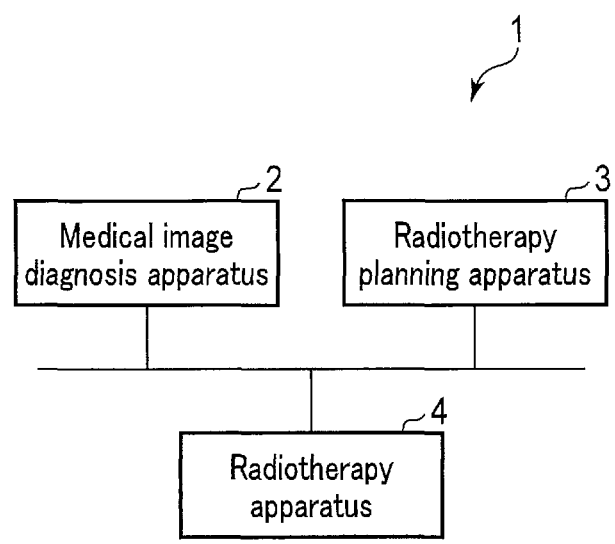
FIG. 1 is a diagram showing a configuration example of a radiotherapy system according to an embodiment.

Hereinafter, a configuration of a radiotherapy system according to the present embodiment will be described with reference to the accompanying drawings. As shown in FIG. 1, the radiotherapy system 1 has a medical image diagnostic apparatus 2, a radiotherapy planning apparatus 3, and a radiotherapy apparatus 4. The medical image diagnostic apparatus 2, the radiotherapy planning apparatus 3, and the radiotherapy apparatus 4 are connected to each other via a network in such a manner that they can communicate with each other. The radiotherapy system 1 is a system with which a therapeutic plan relating to radiotherapy for a patient is produced and radiotherapy is performed in accordance with the therapy plan.

The medical image diagnostic apparatus 2 performs medical imaging on a patient who is a target for therapy, to produce a medical image used for therapy planning. A medical image may be a two-dimensional image including a plurality of two-dimensionally arranged pixels, or a three-dimensional image including a plurality of three-dimensionally arranged voxels. The medical image diagnostic apparatus 2 may be any type of modality capable of generating a medical image. Examples of a modality apparatus are an X-ray computed tomography apparatus, a magnetic resonance imaging apparatus, a cone beam CT apparatus, and a nuclear medicine diagnostic apparatus.

The radiotherapy planning apparatus 3 produces a therapeutic plan for radiation using medical images produced by the medical image diagnostic apparatus 2.

The radiotherapy apparatus 4 performs a therapy on a patient in accordance with the therapeutic plan produced by the radiotherapy planning apparatus 3. The radiotherapy apparatus 4 has a treatment gantry and a treatment bed provided in a treatment room. The treatment bed moves the top plate in such a manner that a treatment targeted body part of the patient approximately matches an isocenter. The treatment gantry supports an irradiation head rotatably around a rotation axis. The irradiation head emits radiation in accordance with the therapeutic plan. Specifically, the irradiation head forms an irradiation field with a multi-divided collimator (multi-leaf collimator) to reduce irradiation on healthy tissue. By irradiating the body part targeted for treatment with radiation, the lesion is annihilated or reduced.

Figure 2:
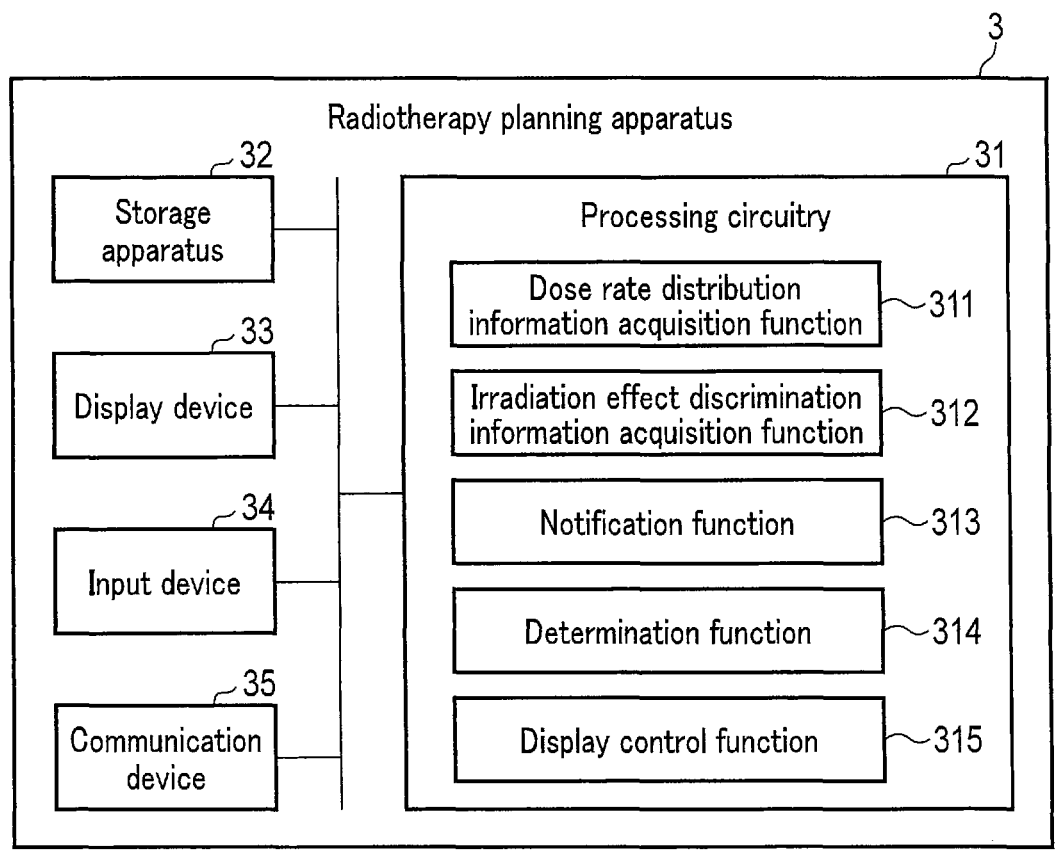
FIG. 2 is a diagram showing a configuration example of a radiotherapy planning apparatus according to the embodiment.

Subsequently, the configuration of the radiotherapy planning apparatus 3 shown in FIG. 1 is explained with reference to FIG. 2. The radiotherapy planning apparatus 3 includes processing circuitry 31, a storage apparatus 32, a display device 33, an input device 34, and a communication device 35.

Figure 3:
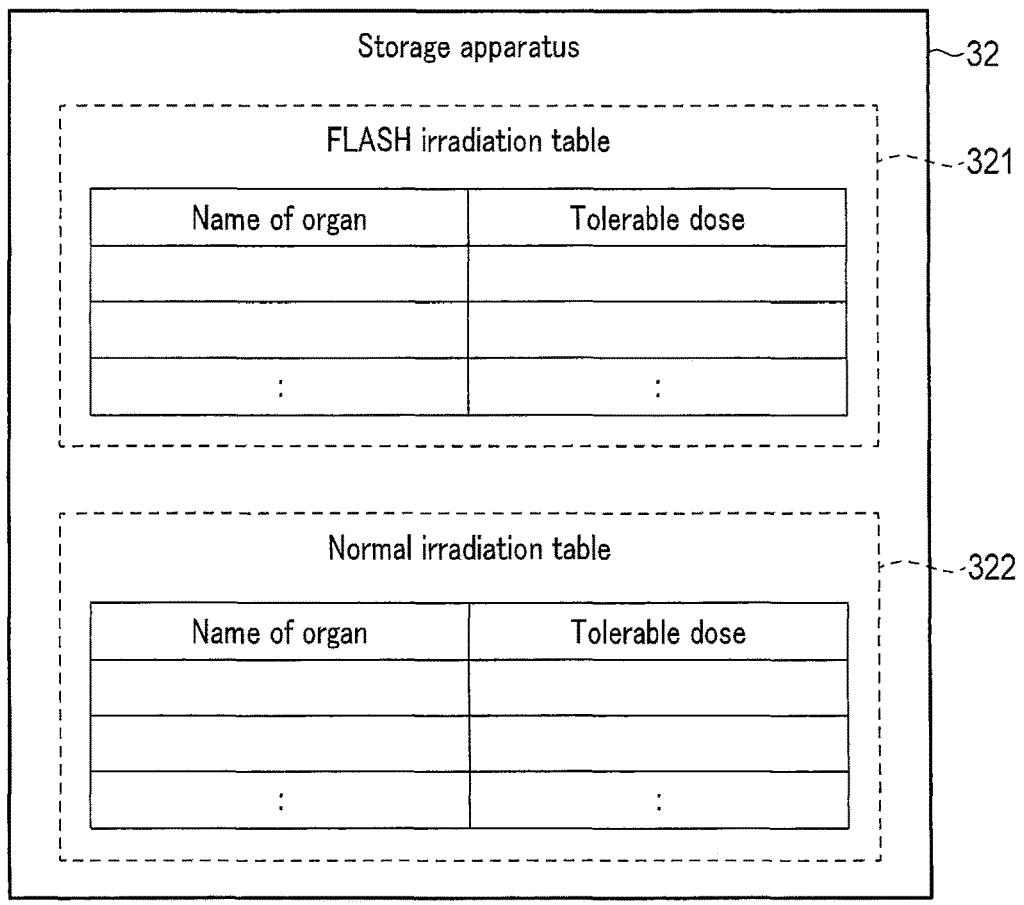
FIG. 3 is a schematic view for explaining a FLASH irradiation table and a normal irradiation table.

The storage apparatus 32 is configured by a storage apparatus such as a ROM (read only memory), an HDD (Hard Disk Drive), or an SSD (Solid State Drive), etc. The storage apparatus 32 stores various types of programs and various types of data. For example, as shown in FIG. 3, the storage apparatus 32 stores a FLASH irradiation table 321 and a normal irradiation table 322. The FLASH irradiation table 321 describes names of organs, each associated with a tolerable dose in the FLASH radiotherapy. The normal irradiation table 322 describes names of organs, each associated with a tolerable dose in the normal radiotherapy. The storage apparatus 32 may store an attenuation rate table that describes an attenuation rate of radiation in a depth direction from the body surface for each direction of irradiation against a human body.

The display device 33 is configured by a display device, such as a liquid crystal display (LCD), a cathode ray tube (CRT) display, an organic electro luminescence display (OELD), etc. The display device 33 displays various types of information under the control of the processing circuitry 31. The display device 33 is an example of a display unit.

The input device 34 is configured by an input interface device, such as a mouse, a keyboard, a trackball, a switch, a button, a joystick, a touch pad, or a touch panel display, etc. The input device 34 accepts various input operations from a user and supplies an electric signal corresponding to the accepted input operation to the processing circuitry 31.

The communication device 35 is configured by a communication interface device that performs a network communication, such as a network interface card (NIC), etc. The communication device 35 receives medical images supplied from the medical image diagnostic apparatus 2. The communication device 35 transmits therapeutic plans to the radiotherapy apparatus 4.

The processing circuitry 31 includes a processor configured by a CPU (central processing unit) or a GPU (graphics processing unit), etc. The processing circuitry 31 controls each unit in the radiotherapy planning apparatus 3 to control the entire radiotherapy planning apparatus 3. The processing circuitry 31 executes a program stored in the storage apparatus 32 so as to realize a dose rate distribution information acquisition function 311, an irradiation effect discrimination information acquisition function 312, a notification function 313, a determination function 314, and a display control function 315. The dose rate distribution information acquisition function 311 and the processing circuitry 31 are examples of a dose rate distribution information acquisition unit. The irradiation effect discrimination information acquisition function 312 and the processing circuitry 31 are examples of an irradiation effect discrimination information acquisition unit. The notification function 313 and the processing circuitry 31 are examples of a notification unit. The determination function 314 and the processing circuitry 31 are examples of a determination unit. The display control function 315 and the processing circuitry 31 are examples of a display control unit. Each of the functions 311-315 may be partially or entirely configured by an integrated circuit, such as an application specific integrated circuit (ASIC), for example.

The radiotherapy planning apparatus 3 configured in this manner produces a radiotherapy plan. A high dose-rate radiation in which radiation is applied at an extremely high dose rate (for example, 40 Gy/sec) compared to a conventional dose rate (for example, 0.03 Gy/sec) in a short time (called "FLASH radiotherapy") is known in the field of radiotherapy. With FLASH radiotherapy, a targeted tumor can be treated with minimum damage to healthy tissue (hereinafter, "FLASH irradiation effect"); therefore, FLASH radiotherapy is expected to attain safer radiotherapy with fewer side effects compared to conventional radiotherapy.

Since radiation of electron beams (MeV) or the like attenuates according to a depth in an irradiated body, if a high dose rate needed to attain the FLASH irradiation effect cannot be maintained throughout a FLASH irradiation path (hereinafter, an "irradiation path"), electron beam irradiation may damage healthy tissue. The radiotherapy planning apparatus 3 identifies an area in which the FLASH effect can be attained (a "FLASH area" hereinafter) and an area in which the FLASH effect cannot be attained (a "non-FLASH area" hereinafter) on an irradiation path based on preset irradiation conditions, and shows the identified areas in a distinguishable manner. A FLASH area is an example of a first area. A non-FLASH area is an example of a second area.

Figure 4:
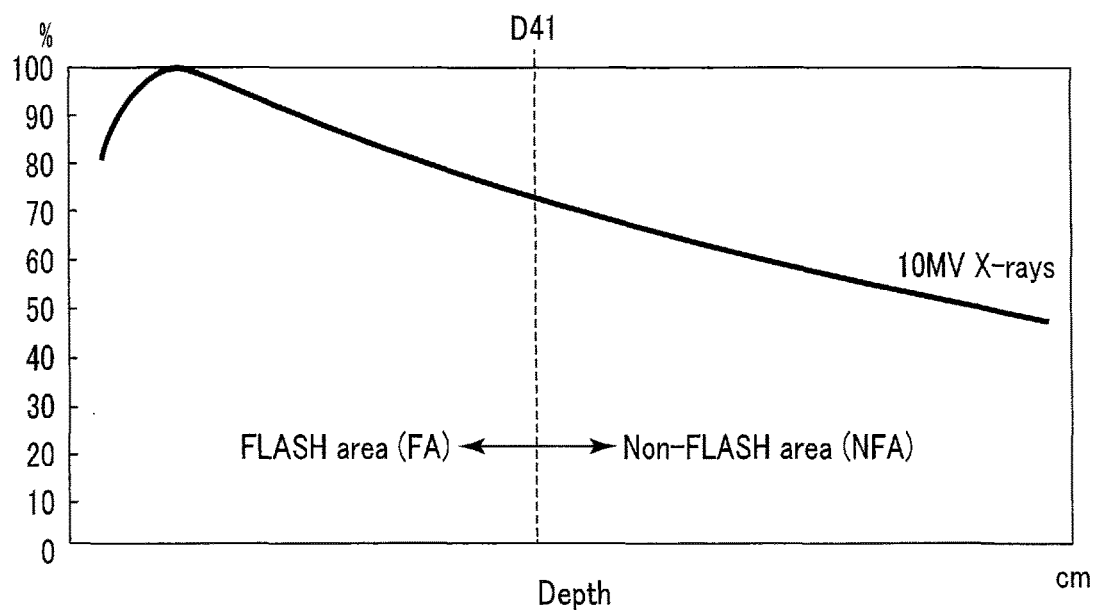
FIG. 4 is a diagram showing a depth where a FLASH area is separated from a non-FLASH area based on attenuation of X-rays a depth at which X-ray attenuation separates FLASH and non-FLASH areas.

Herein, a FLASH area and a non-FLASH area are explained with reference to FIG. 4. FIG. 4 is a diagram showing an example of a dose rate distribution in a depth direction corresponding to X-ray attenuation, and shows a depth D41 at which a FLASH area FA is separated from a non-FLASH area NFA by X-ray attenuation. The vertical axis represents a relative dose [%]. The horizontal axis represents an irradiation depth of radiation, specifically a depth [cm] from a radiation entrance position (body surface). The relative dose changes in accordance with radiation attenuation along the depth direction (e.g., an attenuation rate).

In FIG. 4, the higher the energy of an X-ray is, the deeper the peak of the dose reaches. The X-ray shown in FIG. 4 attenuates differently in a human body in accordance with an irradiation direction; thus, the depth with which the FLASH effect can be attained varies between irradiation directions. The FLASH irradiation is irradiation of radiation at a high-dose rate (e.g., 40 Gy/sec or higher) in a short time, as explained above. The FLASH effect is an irradiation effect (therapeutic effect) attained by the FLASH irradiation, and an effect of selectively damaging a tumor with minimum damage to healthy tissue. In the present embodiment, the FLASH area in which the FLASH effect can be attained and the non-FLASH area in which the FLASH effect cannot be attained are identified by attenuation. In the embodiment, given that the attenuation increases according to a depth from an entrance position, the non-FLASH area in which the FLASH effect cannot be attained can be identified based on the depth or the attenuation.

For example, FIG. 4 shows a depth D41 at which the FLASH area FA and the non-FLASH area NFA are separated by the attenuation of X-rays, in an irradiation direction. The depth D41 can be determined based on a value of a relative dose (e.g., 70%). At the same time, the FLASH area FA and the non-FLASH area NFA may be identified based on a depth D41 from the entrance position of the X-rays or an attenuation of a dose from the entrance position (an attenuation rate or a value of a relative dose).

Since the dose rate of the area deeper than the depth D41 indicated in FIG. 4 is lower than that of the FLASH irradiation, the FLASH effect cannot be attained; therefore, this area is determined to be a non-FLASH area NFA. In such a non-FLASH area NFA, damage to healthy tissue may not be appropriately suppressed.

Next, an example of an operation of the radiotherapy planning apparatus 3 is explained. Assume a medical image in the following explanations is a three-dimensional CT image collected by an X-ray computed tomography apparatus.

Figure 5:
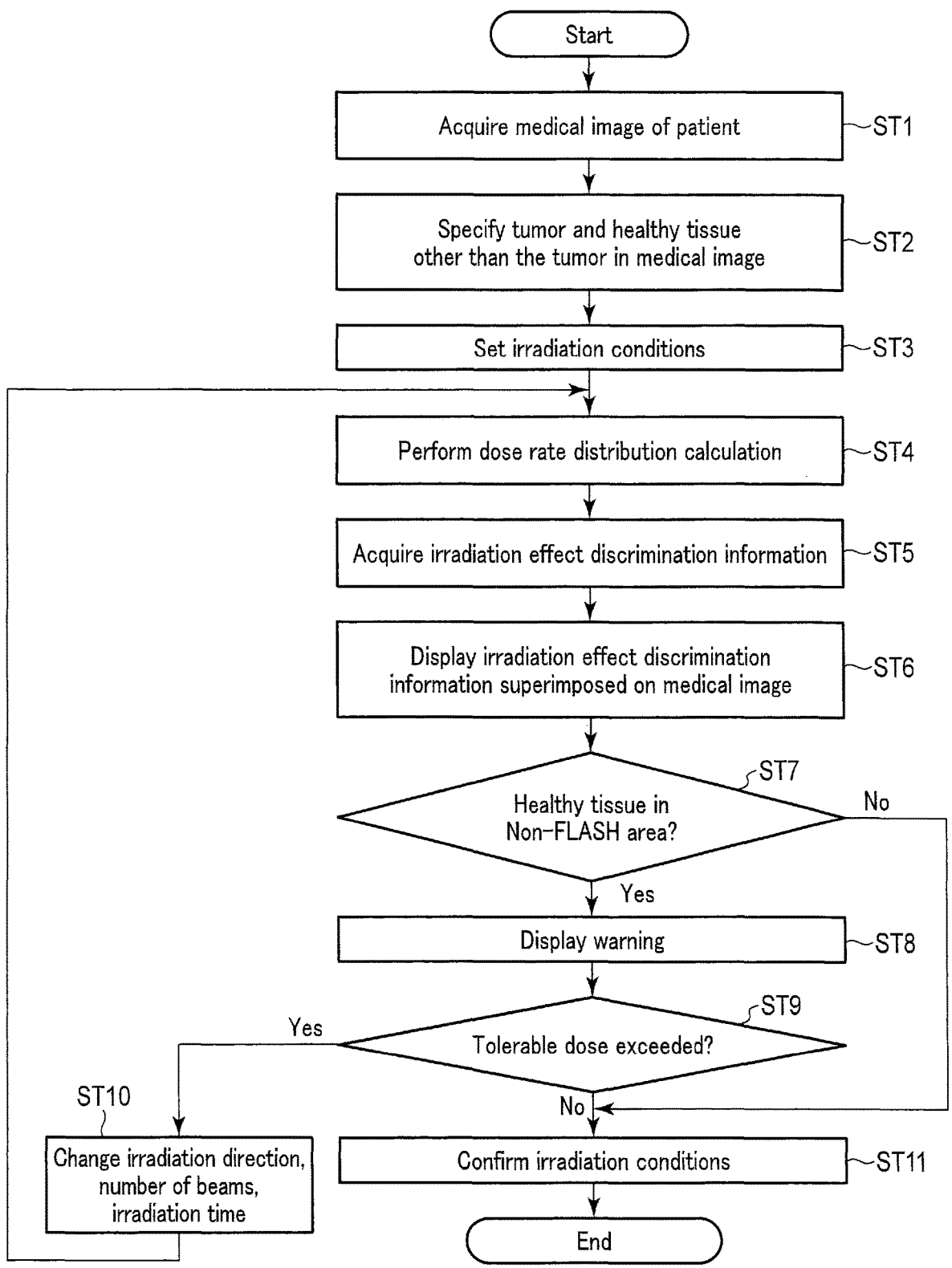
FIG. 5 is a diagram showing a typical flow of a therapy planning process by the radiotherapy planning apparatus.

FIG. 5 is a diagram showing a typical flow of a therapy planning process by the radiotherapy planning apparatus 3. The processing circuitry 31 acquires a medical image of a patient (step ST1). For example, the processing circuitry 31 acquires medical image data received from the medical image diagnostic apparatus 2. In a medical image acquired in step ST1, anatomical structures of the patient are drawn.

After step ST1, the processing circuitry 31 specifies a tumor and healthy tissue other than tumors in the medical image acquired in step ST1 (step ST2). A tumor is a target of radiotherapy. Healthy tissue other than tumors is normal healthy tissue and organs-at-risk. An organ-at-risk is an organ having a high radiation sensitivity and included in healthy tissue. For example, if a tumor is prostate cancer, the organ-at-risk is a rectum and a bladder, etc. Normal healthy tissue is healthy tissue other than an organ-at-risk. It suffices that these areas are specified with a discretionarily chosen method. For example, the areas may be specified manually by a user. The specifying process is performed with the following procedures. First, the processing circuitry 31 causes the display device 33 to display a medical image. A user draws outlines with the input device 34 such as a mouse or a tablet pen, etc. around each of a tumor, normal healthy tissue and an organ-at-risk that are drawn out in the medical image. The processing circuitry 31 specifies the image areas surrounded by the outlines as a tumor, normal healthy tissue, or an organ-at-risk. If there are multiple tumor areas, normal healthy tissue areas, and organs-at-risk, they are individually specified. As an outline of a tumor, a gross tumor volume (GTV) and a clinical target volume (CTV) may be delineated. A tumor may be specified as an area of an internal target volume (ITV), which is a volume that includes a clinical target volume CTV and an internal margin IM (aspiratory movement and peristaltic movement). A tumor may be specified as an area of a planning target volume (PTV) that includes an ITV and a setup margin (SM). Similarly, an organ-at-risk may be specified as an ITV or a PTV. In this case, an organ-at-risk may be called a planning organ-at-risk volume (PRV).

The specifying method is not limited to the above-described method and this specifying process may be automatically performed by image processing. For example, the processing circuitry 31 is able to specify a tumor, normal healthy tissue, and an organ-at-risk by performing threshold processing or image recognition processing on a medical image. The processing circuitry 31 may store information indicating a relationship between an irradiation depth of radiation and an attenuation rate of the radiation in the storage apparatus 32. For example, the processing circuitry 31 obtains an attenuation rate table which describes an attenuation rate of radiation in a depth direction for each irradiation direction of radiation against a human body, and has the storage apparatus 32 store the table. The irradiation directions in the attenuation rate table may be every one degree, five degrees, or ten degrees, or at any discretionarily determined intervals. The attenuation rate of an irradiation direction not described in the attenuation rate table is calculable by interpolation. The attenuation rates in the depth direction in the attenuation rate table may be described at a depth of every 1 mm or 0.5 mm, or any discretionarily determined interval. The attenuation rate may be actually measured by a phantom or a detector or simulated by a computer. The attenuation rate varies, however, according to the internal structure of a human body; for this reason, if the attenuation rate is based on an actual body structure of a patient as in the case where the attenuation rate is determined from a three-dimensional CT image of a patient, the attenuation rate would be more accurate. For example, if a three-dimensional CT image (three-dimensional volume data) of a patient is acquired, the attenuation rate can be calculated from an accumulated value of CT values of X-rays in the three-dimensional volume data.

After step ST2, the processing circuitry 31 sets provisional irradiation conditions for the FLASH irradiation (high-dose rate irradiation) (step ST3). In step ST3, the processing circuitry 31 sets, as irradiation conditions, an irradiation field, an irradiation direction, a dose, and a dose rate. An irradiation field is an area on which radiation is irradiated and is set at least in a medical image. The irradiation direction is a direction of irradiation. The irradiation direction is defined by an angle with respect to the rotation center axis of the treatment gantry of the radiotherapy apparatus 4. The dose is defined as a total dose of irradiation during radiotherapy which is conducted over a few days. The dose rate is defined by a dose per unit of time. In the case of FLASH irradiation, the dose rate is set to a much higher dose rate (e.g., 40 Gy/sec) than a conventional dose rate (e.g., 0.03 Gy/sec). The dose may be called an "irradiation dose", and the dose rate may be called an "irradiation dose rate". The dose and the dose rate may be called an "irradiation dose index value".

In step ST3, the processing circuitry 31 determines a temporary attenuation rate of radiation in a depth direction based on the set irradiation conditions. For example, the processing circuitry 31 searches the attenuation rate table in the storage apparatus 32 based on the set irradiation direction to determine an attenuation rate in a depth direction. The attenuation rate of an irradiation direction not described in the attenuation rate table is calculated by interpolation.

In step ST3, the processing circuitry 31 determines temporary positions of normal healthy tissue, an organ-at-risk, and a tumor, which are located on an irradiation path of radiation, in a three-dimensional CT image, based on the set irradiation conditions. The processing circuitry 31 adjusts an irradiation direction and the number of beams so as to minimize the dose attenuation up to the tumor, avoiding the organ-at-risk. There is a case where radiation greatly attenuates even when the distance on the irradiation path is short, like in the case where bones are located on the irradiation path; for this reason, an irradiation direction and the number of beams are adjusted based on an attenuation rate, not on a distance, in step ST3. After this adjustment, step ST3 is finished.

After step ST3, the processing circuitry 31 performs a dose rate distribution calculation to acquire dose rate distribution information indicating distribution of a dose rate in the irradiation path of the radiation based on the irradiation conditions that were set in step ST3 (step ST4). In step ST4, the processing circuitry 31 may acquire dose rate distribution information based on, for example, the irradiation conditions of the radiation and information indicating a relationship between an irradiation depth and an attenuation rate of the radiation. In step ST4, the processing circuitry 31 may generate spatial distribution of a predicted dose rate in accordance with a discretionarily selected dose calculation algorithm based on the irradiation conditions and the medical image. The predicted dose rate is calculated as a predicted value of an administered dose rate relating to a single FLASH irradiation. As a dose calculation algorithm, an equivalent TAR (tissue-air ratio) method, a differential scattering air dose ratio method, a micro volume method, a Monte Carlo method, and a convolution method, etc. are available, for example. The processing circuitry 31 may use a trained model which is trained through machine learning to output dose rate distribution information indicating dose rate distribution on an irradiation path of radiation in response to an input of irradiation conditions of the radiation. In this case, the processing circuitry 31 may acquire dose rate distribution information by reading a trained model from the storage apparatus 32 and operating the trained model. Alternatively, the processing circuitry 31 may acquire dose rate distribution information through a configuration, like an ASIC or an FPGA, in which a trained model is implemented in a processor circuit. The trained model is a trained machine learning model generated by having a machine learning model perform machine learning based on training data, for example.

After step ST4, the processing circuitry 31 acquires irradiation effect discrimination information for discriminating irradiation effects of radiation on an irradiation path based on the acquired dose rate distribution information (step ST5). Specifically, for example, the processing circuitry 31 may acquire irradiation effect discrimination information based on a comparison between a dose rate represented by the acquired dose rate distribution information and a predetermined threshold. Herein, the irradiation effect discrimination information is information discriminating the effects of short-time and high dose-rate irradiation. For example, the irradiation effect discrimination information may be information discriminating between the FLASH area FA in which the irradiation effects can be attained and the non-FLASH area NFA in which the irradiation effects cannot be attained in the irradiation path. The FLASH area FA and the non-FLASH area NFA constitute an irradiation path of radiation. The irradiation path may be called a beam path. To give a supplementary explanation, the irradiation path may be either the FLASH area or the non-FLASH area at a certain depth in a body. For example, in the case of X-ray irradiation, the irradiation path is the FLASH area along the depth direction of the body up to a depth where the dose rate reaches a threshold of an attenuation level. Such an irradiation path is the same in the case where gamma rays or electron beams are irradiated instead of X-rays. In the case of irradiation proton rays or carbon ion beams instead of X-rays, the irradiation path is an area in which a dose increases along the depth direction of the body and there is the FLASH area only in the part where the dose rate exceeds a threshold.

Figure 6:
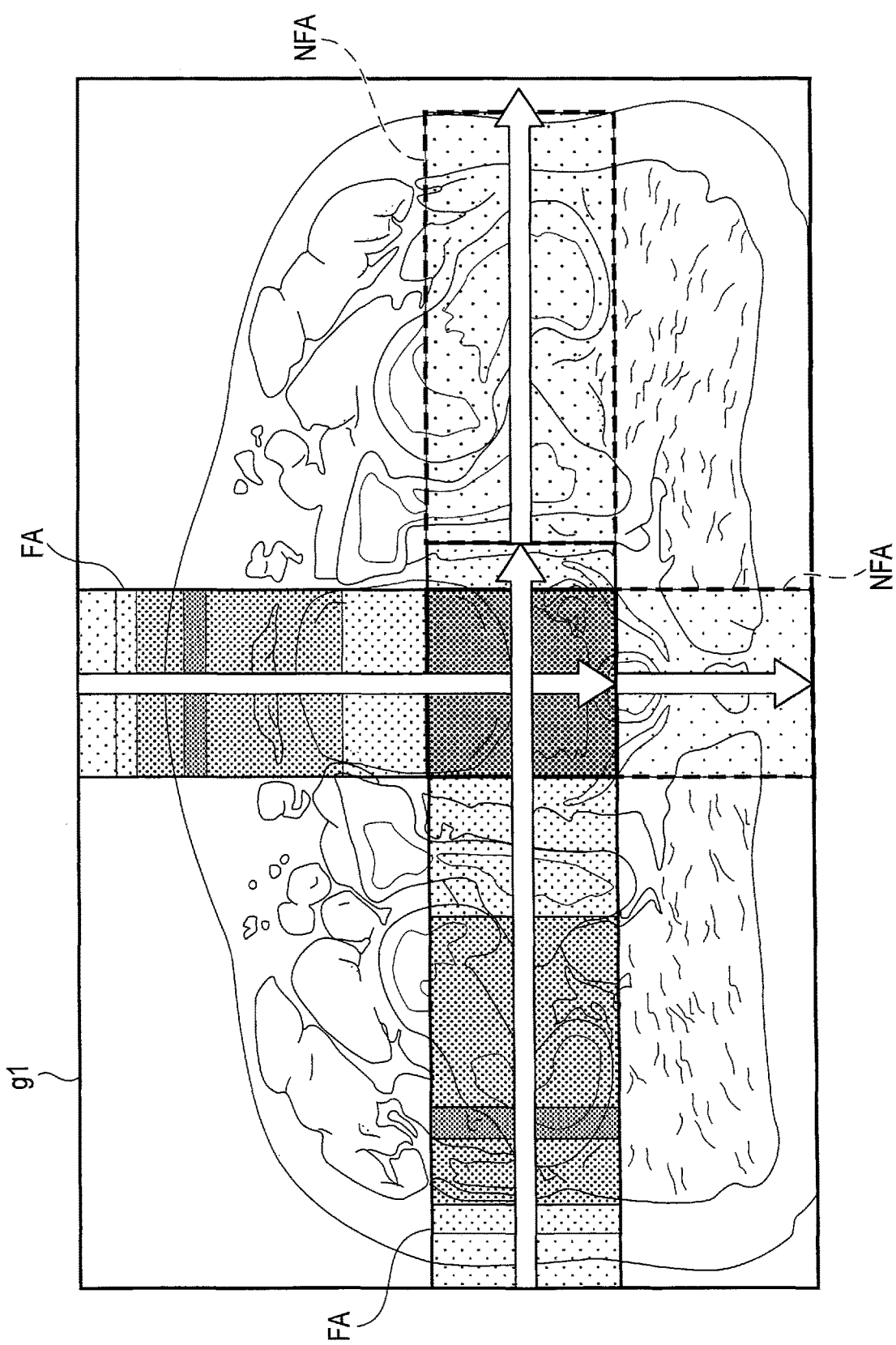
FIG. 6 is a diagram showing a display example where the FLASH area and the non-FLASH area are superimposed on a medical image.
Figure 7:
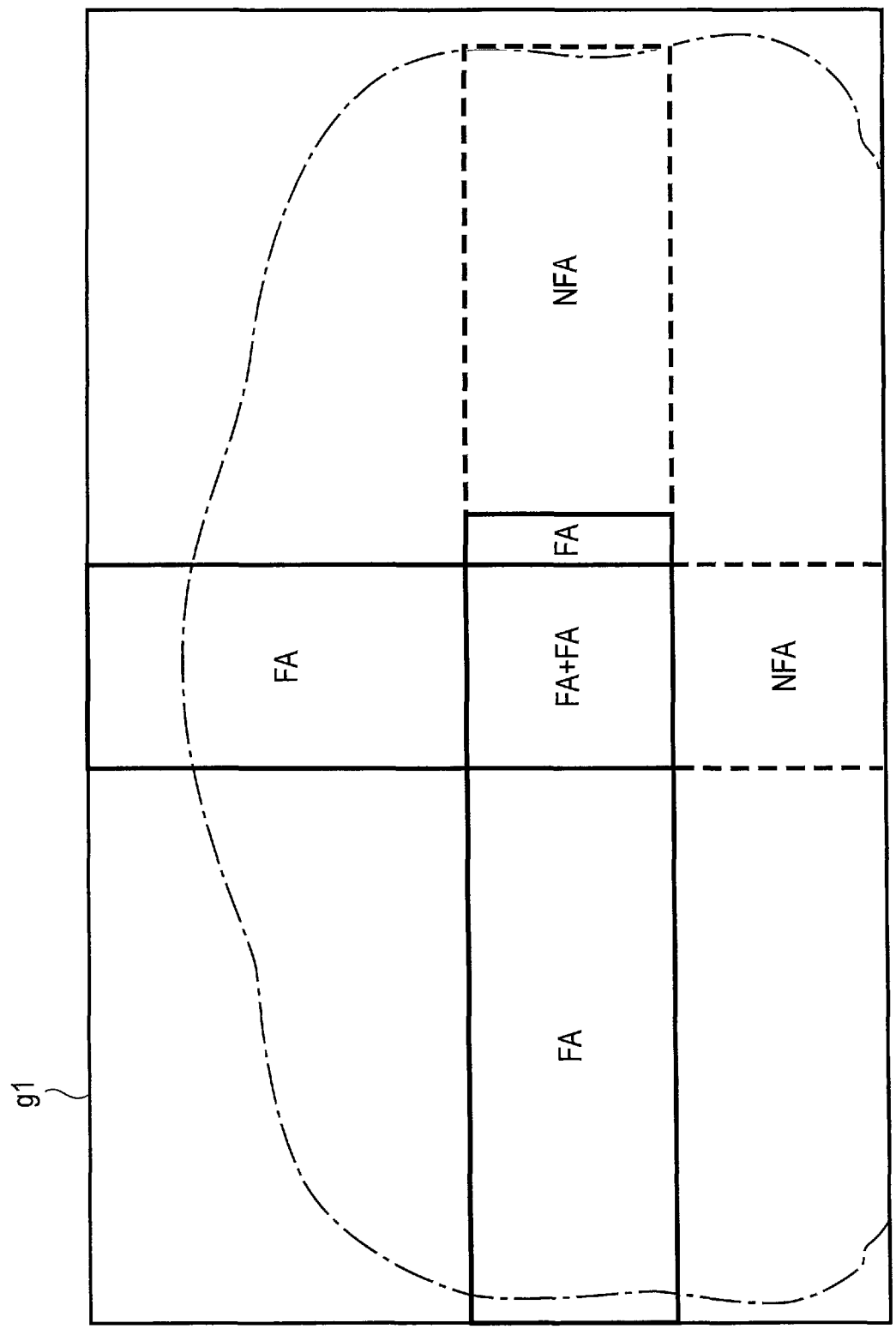
FIG. 7 is a schematic view for explaining the FLASH area and the non-FLASH area in FIG. 6.
Figure 8:
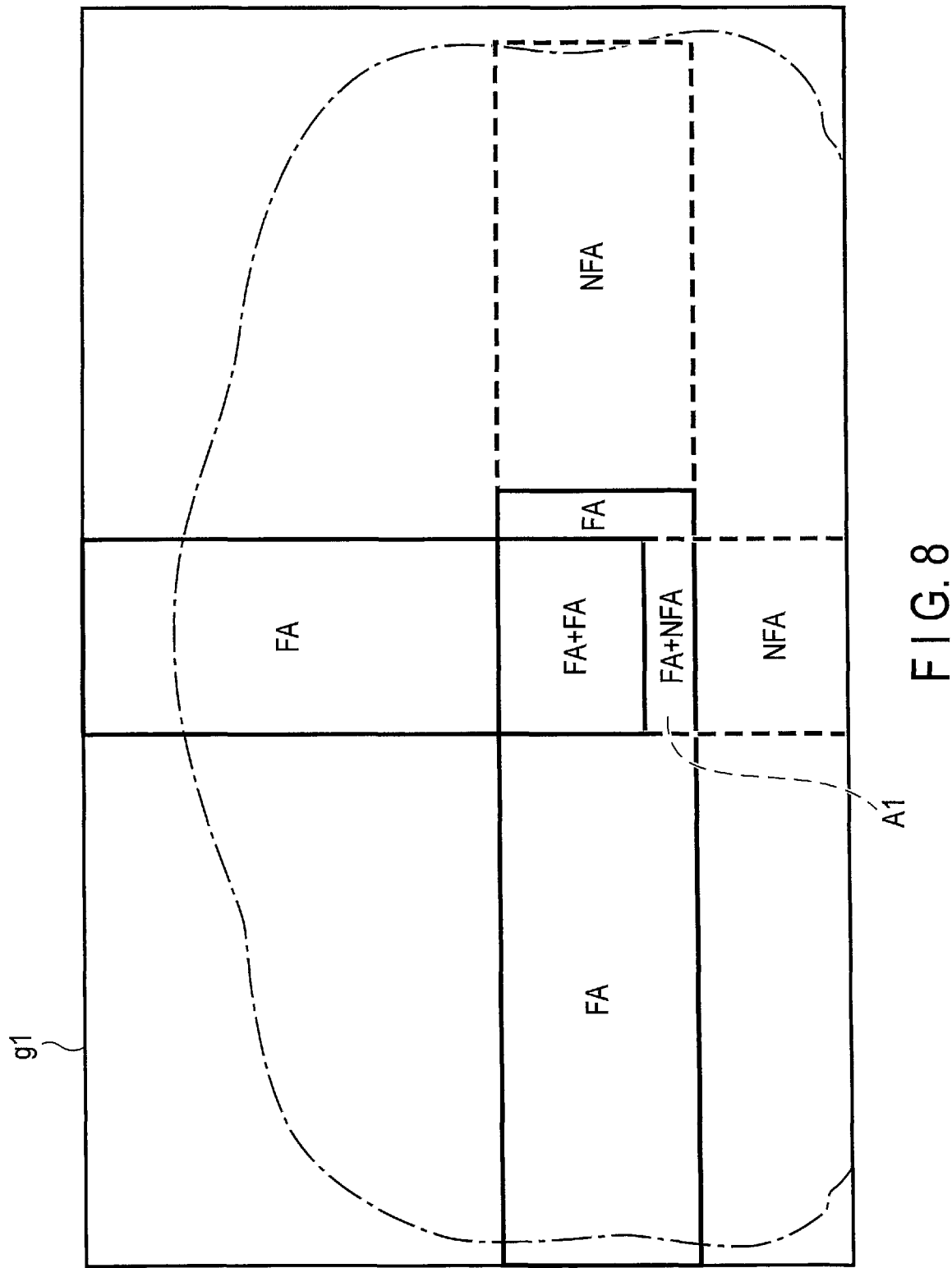
FIG. 8 is a schematic view for supplementary explanation of the FLASH area and the non-FLASH area in FIG. 7.

After step ST5, the processing circuitry 31 causes the display device 33 to display a medical image g1 of a patient on which the dose rate distribution calculation result and the irradiation effect discrimination information for discriminating between the FLASH area FA and the non-FLASH area NFA are superimposed, as shown in FIG. 6 (step ST6). Herein, the calculation result of dose rate distribution in the FLASH area FA is thickly shaded in accordance with a relatively high dose rate, and the calculation result of dose rate distribution in the non-FLASH area NFA is thinly shaded in accordance with a relatively low dose rate. In reality, such dose rate distribution calculation results are color-coded in accordance with dose rate distribution. In FIG. 6, the irradiation effect discrimination information includes a solid-line frame for identifying the FLASH area FA and a dashed-line frame for identifying the non-FLASH area NFA. In addition to these frames, the irradiation effect discrimination information may include an arrow for identifying the FLASH area FA and an arrow for identifying the non-FLASH area NFA. These two arrows may be displayed in different colors. The irradiation path consisting of the FLASH area FA and the non-FLASH area NFA as shown in FIG. 6 is distributed in approximately a cross-like shape, as shown in FIG. 7. In FIG. 7, the approximately center part of the medical image g1 is an area where the FLASH area FA in the irradiation path at the irradiation direction of 0 degrees overlaps the FLASH area FA in the irradiation path at the irradiation direction of 270 degrees (shown as "FA+FA" in FIG. 7). To give supplementary explanation, if the irradiation path at the irradiation direction of 270 degrees is located with a deviation of 0 degrees in a depth direction of the irradiation path of the irradiation direction, there will be an area A1 where the FLASH area FA and the non-FLASH area FA overlap, as shown in FIG. 8 ("FA+NFA" in FIG. 8). The area A1 becomes a non-FLASH area due to the influence of the non-FLASH area NFA in one of the irradiation paths; as a consequence, the FLASH effects cannot be sufficiently attained. As a result of this, if there is an area where the FLASH area of one of the irradiation paths overlaps the non-FLASH area of the other irradiation path, the processing circuitry 31 may identify the area as the non-FLASH area in which no FLASH effects can be attained. The irradiation effect discrimination information for discriminating between the FLASH area and the non-FLASH area may be superimposed on a different image. For example, the processing circuitry 31 may superimpose the irradiation effect discrimination information on a phantom image or a computer simulation image, instead of the medical image g1. In other words, the processing circuitry 31 may cause the display device 33 to display the irradiation effect discrimination information superimposed on a phantom image or a computer simulation image.

After step ST6, the processing circuitry 31 determines whether or not healthy tissue (normal healthy tissue and/or an organ-at-risk) is located at a position corresponding to the non-FLASH area NFA identified in the irradiation effect discrimination information in step ST5 (step ST7). As a result of the determination, if no healthy tissue is located, the processing circuitry 31 transfers to step ST11.

As a result of step ST7, if healthy tissue is located at a position corresponding to the non-FLASH area NFA, on the other hand, the processing circuitry 31 causes the display device 33 to display a warning to prompt changing of the irradiation conditions (step ST8). As a warning, an emphasized display of healthy tissue or a warning message is usable as appropriate. As an emphasized display of healthy tissue, for example a color-changing display or a flashing display are usable as appropriate. As an alert message, a sentence for prompting changing of the irradiation conditions, such as "there is an organ-at-risk in the non-FLASH area NFA" or "there is normal healthy tissue in the non-FLASH area NFA", may be used. Alternatively, a word, such as "warning", may be displayed as a warning message to prompt changing of the irradiation conditions. In order to clearly indicate a warning target, however, it is preferable to use a single word as a warning message along with an emphasized display of normal healthy tissue and/or an organ-at-risk.

After step ST8, if healthy tissue is located at a position corresponding to the non-FLASH area, the processing circuitry 31 determines whether or not the tolerable dose of the healthy tissue is exceeded by the irradiation (step ST9). For example, the processing circuitry 31 may perform the determination based on a tolerable dose corresponding to the name of the organ-at-risk by referring to the FLASH irradiation table 321 in the storage apparatus 32. As a result of the determination, if the tolerable dose is exceeded, the processing circuitry 31 proceeds to step ST10.

In the above example, a tolerable dose is used as an index of a dose applied to the organ-at-risk; however, an index of a dose volume histogram (DVH), which is widely used in the field of therapy planning, may be used.

As a result of the determination in step ST9, the processing circuitry 31 notifies a user of the information based on the determination result and sets new irradiation conditions (step ST10). In other words, the processing circuitry 31 causes the display device 33 to display a warning indicating that the tolerable dose is exceeded, and changes the irradiation conditions, such as the irradiation field, the irradiation direction, the dose, and the dose rate, etc., in accordance with a user's instructions via the input device 34 or a predetermined algorithm. If a dose rate (Gy/sec) is changed, the value of a dose rate may be directly changed, and a value of the dose rate may be indirectly changed by the change of an irradiation time (sec). The processing circuitry 31 may change the irradiation direction, the number of beams, and the irradiation time as shown in (a) and (b) below, for example. In other words, the processing circuitry 31 changes (a) the irradiation direction, the number of beams, or the irradiation time (step ST10), and updates the dose rate distribution calculation result and the irradiation effect discrimination information in accordance with the change (steps ST4 and ST5). Alternatively, the processing circuitry 31 (b) updates the beam direction, the number of beams, and the irradiation time upon designation by the input device 34 of an area for which the FLASH area FA is desired. In either case, after step ST10, the processing circuitry 31 performs steps ST4 to ST9 in the above-described manner based on the changed irradiation conditions. The loop that starts from step ST10 and returns to ST10 through ST4 to ST9 is repeated until it is determined that healthy tissue is not located at a predetermined position in step ST7 or it is determined that the dose is equal to or lower than the tolerable dose in step ST9.

If it is determined that healthy tissue is not located at a predetermined position in step ST7, or if it is determined in step ST9 that the tolerable dose is not exceeded, the processing circuitry 31 sets the irradiation conditions that were set in the most recent step ST3 or ST10 as a confirmed version (step ST11).

As described above, the processing circuitry 31 can search for irradiation conditions for performing appropriate FLASH irradiation by performing steps ST3 to ST11. The irradiation conditions of the confirmed version are stored in the storage apparatus 32. Thereafter, the processing circuitry 31 generates radiotherapy plan data and transmits the data to the radiotherapy apparatus 4. The radiotherapy plan data includes, for example, data of the superimposed image displayed in step ST6 and the irradiation conditions that are set in step ST11.

After transmitting the radiotherapy plan data, the therapy planning by the radiotherapy planning apparatus 3 is finished. Thereafter, the radiotherapy apparatus 4 irradiates the patient with radiation in accordance with the radiotherapy plan data to conduct radiotherapy.

As described above, according to the embodiment, dose rate distribution information indicating a dose rate in an irradiation path of radiation is acquired based on irradiation conditions of the radiation, and irradiation effect discrimination information for discriminating irradiation effects of radiation in an irradiation path is acquired based on the acquired dose rate distribution information. It is thus possible to clearly identify the irradiation effects of radiation in an irradiation path and produce a radiotherapy plan. It is thereby possible to suppress damage to healthy tissue and provide a radiotherapy plan with which irradiation effects can be appropriately attained.

According to the embodiment, dose rate distribution information may be acquired based on the irradiation conditions relating to radiation and information indicating a relationship between an irradiation depth of the radiation and an attenuation rate of the radiation. In this case, in addition to the above-described advantageous effects, it is possible to acquire dose rate distribution information more easily.

According to the embodiment, the irradiation effect discrimination information to be acquired may be information for discriminating irradiation effects of high-dose radiation applied for a short time. In this case, it is possible to acquire dose rate distribution information for discriminating FLASH irradiation effects, in addition to the above-described advantageous effects.

According to the embodiment, irradiation effect discrimination information may be acquired based on a comparison between a dose rate represented by the acquired dose rate distribution information and a predetermined threshold. In this case, in addition to the above-described advantageous effects, it is possible to acquire irradiation effect discrimination information in accordance with a threshold value of a dose rate.

According to the embodiment, the irradiation effect discrimination information to be acquired may be information discriminating between a first area in which the irradiation effects can be attained and a second area in which the irradiation effects cannot be attained, in an irradiation path. In this case, it is possible to clearly discriminate, in an irradiation path, between the first area in which the irradiation effects can be attained and the second area in which the irradiation effects cannot be attained, in addition to the above-described advantageous effects.

According to the embodiment, in the case where healthy tissue is located at a position corresponding to the second area, the changing of irradiation conditions may be prompted. In this case, in addition to the above-described advantageous effects, it is possible to change the irradiation conditions so as to exclude healthy tissue from the second area from which no irradiation effects can be attained.

According to the embodiment, the processing may be configured to determine, when healthy tissue is located at a position corresponding to the second area, whether or not the tolerable dose of the healthy tissue is exceeded by irradiation of radiation, and to report information based on the determination result. In this case, in addition to the above-described operation effects, it is possible to confirm that the tolerable dose of the healthy tissue is not exceeded. It is also possible to avoid a situation where the healthy tissue enters the second area, exceeding the tolerable dose.

According to the embodiment, the acquired irradiation effect discrimination information may be superimposed on a medical image of a subject and displayed on the display unit. In this case, in addition to the above-described effects, it is possible to display irradiation effects of radiation on a medical image in an identifiable manner.

According to the embodiment, in the case where the irradiation conditions are set by specifying an internal target volume ITV of a tumor from a medical image, it is possible to check if the internal target volume ITV of the tumor is located within a first area or not. Furthermore, since the internal target volume ITV of the tumor is a volume that includes an internal margin (aspiratory movement and peristaltic movement), it is possible to negate a need of controlling (gating) to deal with body movement or aspiration-related movement.

According to the embodiment, if there is an area where the first area of one of the irradiation paths overlaps the second area of the other irradiation path, the overlapping area may be identified as the second area in which irradiation effects cannot be attained. In this case, in addition to the above-described advantageous effects, it is possible to prevent an erroneous operation of specifying an area where the first area overlaps the second area as a first area.

The foregoing embodiment may be carried out as in the following modifications.

First Modification of Embodiment

Figure 9:
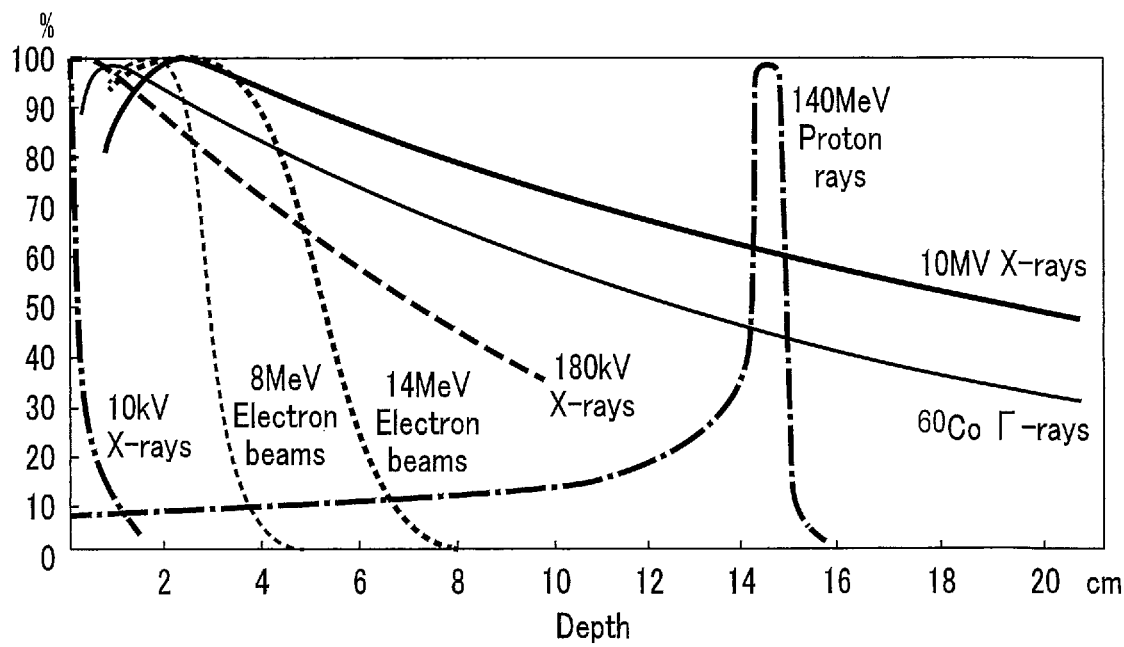
FIG. 9 is a diagram showing an example of dose rate distribution in a depth direction corresponding to attenuation of various types of radiation applicable to the radiotherapy planning apparatus according to a first modification of the embodiment.
Figure 10:
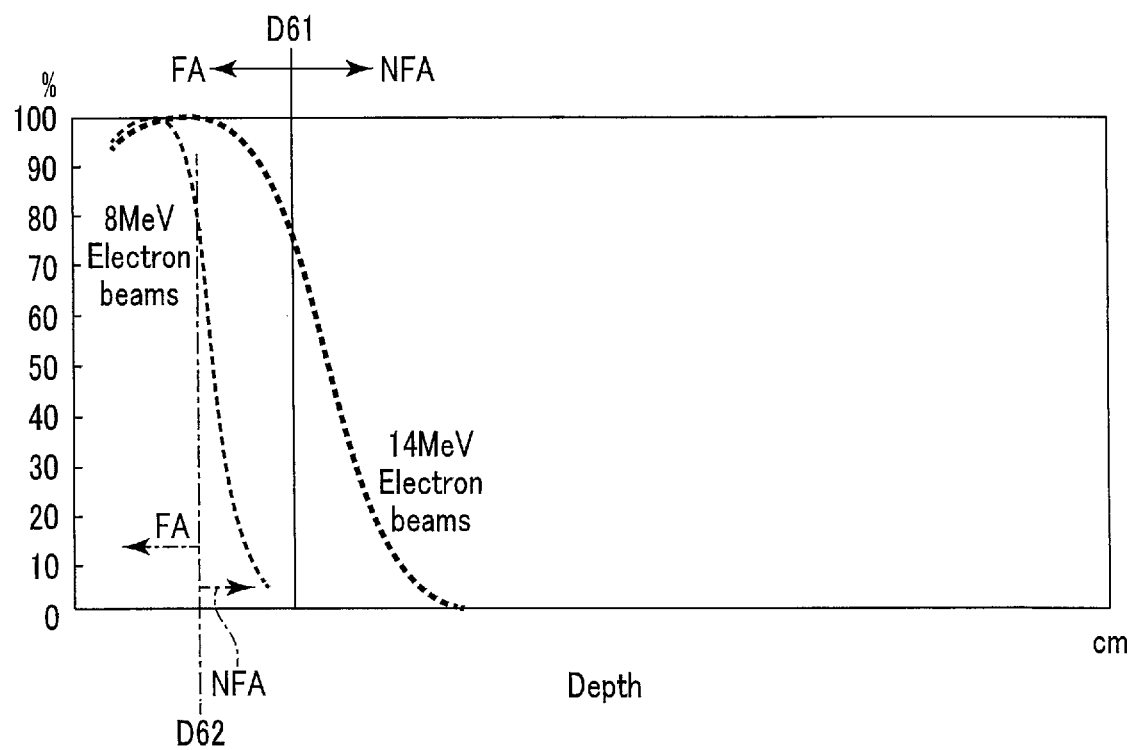
FIG. 10 is a diagram showing a depth at which a FLASH area and a non-FLASH area are separated by attenuation of the electron beams shown in FIG. 9.

A first modification of the embodiment is an aspect wherein radiation other than the X-rays shown in FIG. 4 are irradiated, as shown in FIGS. 9 through 11. Specifically, the embodiment may be modified into the first modification wherein gamma rays, electron beams, proton rays, or carbon ion beams (not shown) are irradiated, instead of X-rays.

FIG. 9 is a diagram showing an example of dose rate distribution in a depth direction corresponding to attenuation of various types of radiation applicable to the radiotherapy planning apparatus according to a first modification of the embodiment. Of the radiation shown in FIG. 9, X-rays and gamma rays are electromagnetic waves, and electron beams and proton rays are particle beams. Particle beams are not limited thereto, and carbon ion beams (not shown) may be applied. In FIG. 9, the vertical axis represents a relative dose [%]. The horizontal axis represents an irradiation depth of radiation, specifically a depth [cm] from a radiation entrance position (body surface). The relative dose changes in accordance with radiation attenuation along the depth direction (e.g., an attenuation rate) in every irradiation direction.

In FIG. 9, the higher the energy of an X-ray and a gamma ray is, the deeper the peak of the dose reaches. Although the peak of electron beams reaches deeper as the energy increases, it only reaches up to a certain depth, unlike X-rays and gamma rays. The proton rays provide a large dose at the terminal end of the range and exhibit the so-called Bragg peak. The various types of radiation shown in FIG. 9 have different patterns of attenuation inside the body; thus, a depth at which the FLASH effects can be attained differs between the types, as shown in FIGS. 10 and 11.

For example, FIG. 10 shows the depths D61 and D62 at which the FLASH area FA and the non-FLASH area NFA are separated by to the attenuation of the 14 MeV electron beams and the 8 MeV electron beams shown in FIG. 9. The depths D61 and D62 can be determined based on a value of a relative dose (e.g., 70%). At the same time, the FLASH area FA and the non-FLASH area NFA may be identified based on depths D61 and D62 from the entrance position of the electron beams or an attenuation of a dose from the entrance position (an attenuation rate or a value of a relative dose).

FIG. 11 shows the depth D71 and D72 where a FLASH area NA and a non-FLASH area NFA are discernable based on the Bragg peak of proton rays in FIG. 9. The depth D71 and D72 can be determined based on a value of a relative dose (e.g., 70%).

In this case, an area shallower than the depth D71 and the area deeper than the depth D72 are the non-FLASH areas NFA. In other words, the FLASH area FA is an area between the depth D71 and the depth D72 in FIG. 11.

At the same time, the FLASH area FA and the non-FLASH area NFA may be identified based on a depth D71 and D72 from the entrance position of the proton ray or an attenuation of a dose from the entrance position (an attenuation rate or a value of a relative dose), regardless of the depth of the Bragg peak.

Since the dose rate of the area deeper than the depth D61 and D62 indicated in FIG. 10 is lower than that of the FLASH irradiation, the FLASH effect cannot be attained; therefore, this area is determined to be a non-FLASH area NFA. In such a non-FLASH area NFA, damage to healthy tissue may not be appropriately suppressed.

According to the first modification of the embodiment, the same advantageous effects as those in the foregoing embodiment can be attained, even when radiation other than X-rays shown in FIG. 4 is applied.

Second Modification of Embodiment

Figure 12:
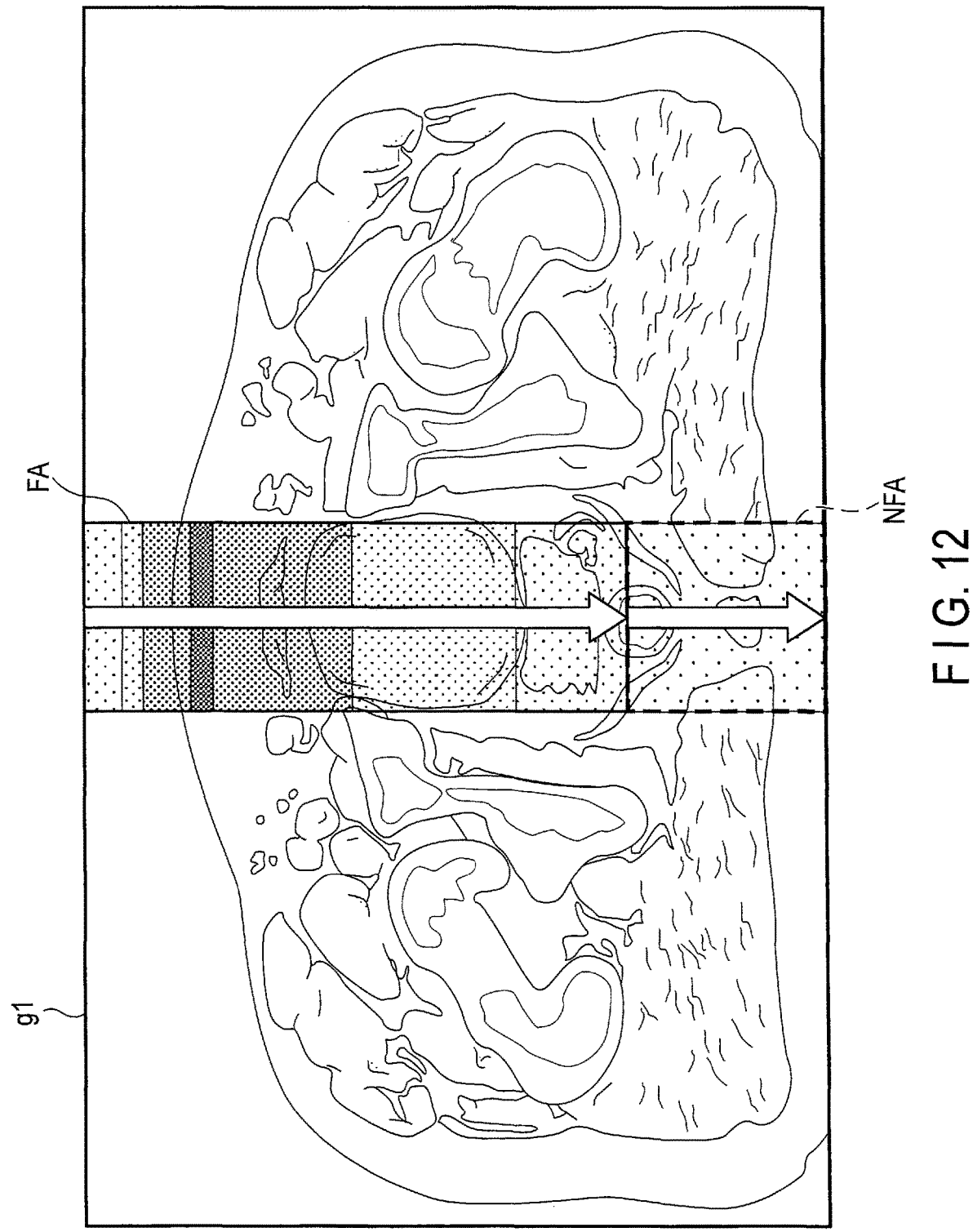
FIG. 12 is a diagram showing a display example where the FLASH area and the non-FLASH area are superimposed on a medical image in a second modification of the embodiment.

The second modification of the embodiment is directed to an aspect of irradiation of X-rays in one irradiation direction, as shown in FIG. 12.

Specifically, in step ST6, the processing circuitry 31 causes the display device 33 to display the medical image g1 on which the dose rate distribution calculation result and the irradiation effect discrimination information for discriminating between the FLASH FA area and the non-FLASH area NFA are superimposed. In FIG. 12, in the approximately center part of the medical image g1, the FLASH area FA is distributed from the body surface along the irradiation path in the "0 degree" irradiation direction, and the non-FLASH area NFA is distributed in an area deeper than the FLASH area FA. Not being limited to the example shown in FIG. 12, it is possible to irradiate X-rays in three or more irradiation directions.

According to the second modification of the embodiment as described above, the same advantageous effects as those in the foregoing embodiment can be attained, even when radiation of X-rays is performed in a single irradiation direction. The second modification may be performed in a combination with the first modification. In other word, the same advantageous effects as those in the foregoing embodiment can be attained, even when radiation other than X-rays is irradiated in a single irradiation direction.

Third Modification of Embodiment

In the third modification of the embodiment, the penumbra area in the irradiation path is identified as a non-FLASH area NFA, and the area other than the non-penumbra area (namely, non-penumbra area) in the irradiation path is identified as a FLASH area FA. A penumbra is radiation that passes through a collimator that restricts an irradiation field, and the dose rate thereof is reduced by a collimator; for this reason, the FLASH effects cannot be attained in the penumbra area.

As an example of the third modification, the processing circuitry 31 specifies a penumbra area and a non-penumbra area by a user's area designation targeting the predetermined area in the medical image. As another example, the processing circuitry 31 specifies a penumbra area by user's area designation that targets the irradiation path in the medical image, and specifies the area other than the penumbra area in the irradiation path as a non-penumbra area. As another example, the processing circuitry 31 specifies a non-penumbra area by a user's area designation that targets the irradiation path in the medical image, and specifies the area other than the non-penumbra area in the irradiation path as a penumbra area. As another example, the processing circuitry 31 may specify a penumbra area and a non-penumbra area in the predetermined area of the medical image based on a parameter defining an irradiation field.

According to the above-described third modification of the embodiment, it is possible to attain the same advantageous effects as those in the foregoing embodiment, even if the penumbra area in the irradiation path is identified as a non-FLASH area NFA, and the area other than the penumbra area (namely, non-penumbra area) in the irradiation path is identified as a FLASH area FA. In addition to that, the non-penumbra area is excluded from the area in the irradiation path identified as the FLASH area FA; for this reason, it is possible to improve the accuracy of specifying the FLASH area FA.

Fourth Modification of Embodiment

The fourth modification of the embodiment is an aspect where a non-FLASH area NFA and a FLASH area FA are identified based at least on one of an irradiation depth of radiation in an irradiation path, radiation absorption characteristics of tissue in the irradiation path, or a penumbra in the irradiation path.

Specifically, the processing circuitry 31 specifies a penumbra area and a non-penumbra area by user's area designation that targets the predetermined area in the medical image. As another example, the processing circuitry 31 specifies a penumbra area by user's area designation targeting the irradiation path in the medical image and specifying the area other than the penumbra area in the irradiation path as a non-penumbra area. As another example, the processing circuitry 31 specifies a non-penumbra area by user's area designation targeting the irradiation path in the medical image and specifying the area other than the penumbra area in the irradiation path as a penumbra area. As another example, the processing circuitry 31 may specify a penumbra area and a non-penumbra area in the irradiation path of the medical image based on a parameter defining an irradiation field.

Next, the processing circuitry 31 calculates a predicted dose rate for each pixel in the irradiation path based on the irradiation conditions. At this time, the processing circuitry 31 calculates, for the penumbra area, a predicted dose rate in consideration of the attenuation of the radiation due to a penumbra. The processing circuitry 31 calculates a predicted dose rate in consideration of at least one of the attenuation rate of radiation according to the irradiation depth in the irradiation path or the attenuation rate of the radiation according to the radiation absorption characteristics of tissue. For the attenuation rate according to the irradiation depth and the radiation absorption characteristics of tissue, experimentally determined values or values calculated by prediction may be used. The processing circuitry 31 identifies an area in which the predicted dose rate falls below a FLASH effect threshold as a non-FLASH area NFA, and identifies an area in which the predicted dose rate exceeds a FLASH effect threshold as a FLASH area FA. The FLASH effect threshold value is defined by a dose rate with which the FLASH effects can be attained.

According to the fourth modification of the embodiment, the same advantageous effects as those in the embodiment can be attained, even when a non-FLASH area NFA and a FLASH area FA are identified based on at least one of an irradiation depth of radiation in an irradiation path, radiation absorption characteristics of tissue in the irradiation path, and a penumbra in an irradiation path. In addition to that, the accuracy of specifying a non-FLASH area NFA and a FLASH area FA can be improved in accordance with which of an irradiation path, radiation absorption characteristics, and a penumbra is considered.

Fifth Modification of Embodiment

The fifth modification of the embodiment is an aspect where some of the irradiation conditions with which it is determined that the tolerable dose is not exceeded are obtained as candidates for irradiation conditions, and an optimal irradiation condition among the obtained irradiation conditions is set as a confirmed version.

Specifically, if it is determined that the tolerable dose is not exceeded in step ST9, the processing circuit 31 obtains the irradiation conditions that have been set in the latest step ST3 or ST10 as irradiation condition candidates. Subsequently, the processing circuitry 31 proceeds to step ST10 and sets new irradiation conditions as described earlier, and performs steps ST4 through ST9 in the above-described manner based on the changed irradiation conditions. The loop starting from and returning to ST10 via steps ST4 through ST9 is repeated until a predetermined number of irradiation condition candidates are obtained.

If the predetermined number of irradiation condition candidates are obtained as a result of the determination in step ST9, the processing circuitry 31 proceeds to step ST11 and confirms an optimal irradiation condition among the predetermined number of irradiation condition candidates. As an optimal irradiation condition, an irradiation condition with which a lowest dose is achieved can be used, for example.

According to the above-described fifth modification of the embodiment, an optimal irradiation condition is obtained from a predetermined number of irradiation condition candidates. It is therefore possible to obtain a more optimal irradiation condition in addition to the advantageous effects achieved in the embodiment.

According to at least one of the foregoing embodiments, it is thereby possible to suppress damage to healthy tissue and provide a radiotherapy plan with which irradiation effects can be appropriately attained.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field. Programmable Gate Array (FPGA)). The processor realizes its function by reading and executing the program stored in the memory. A program may be directly integrated into the circuitry of the processor, instead of storing the program in the memory. In this case, the processor reads and executes a program integrated into the circuitry to realize the corresponding function. The function corresponding to the program may be implemented by a combination of logic circuits instead of executing the program. The processors described in connection with the above embodiments are not limited to single-circuit processors; a plurality of independent processors may be integrated into a single processor that implements the functions of the processors. Furthermore, a plurality of constituent elements shown in FIGS. 1 and 2 may be integrated into one processor to implement the functions.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Regarding the foregoing embodiment, the appendage of the following discloses one aspect and selective features of the invention.

Additional Note 1

A radiotherapy planning apparatus comprising processing circuitry, the processing circuitry configured to:
acquire dose rate distribution information indicating distribution of a dose rate in an irradiation path of radiation based on irradiation conditions of the radiation; and
acquire irradiation effect discrimination information for discriminating irradiation effects of radiation in the irradiation path based on the acquired dose rate distribution information, Additional Note 2

The processing circuitry may acquire the dose rate distribution information based on irradiation conditions of the radiation and information representing a relationship between an irradiation depth of the radiation and an attenuation rate of the radiation.

Additional Note 3

The irradiation effect discrimination information acquired by the processing circuitry may be information for discriminating irradiation effects of short-time, high-dose rate radiation.

Additional Note 4

The processing circuitry may acquire the irradiation effect discrimination information based on a comparison between a dose rate represented by the acquired dose rate distribution information and a predetermined threshold.

Additional Note 5

The irradiation effect discrimination information acquired by the processing circuitry may be information discriminating between the first area in which the irradiation effects can be attained and the second area in which the irradiation effects cannot be attained.

Additional Note 6

The processing circuitry prompts changing of the irradiation conditions when healthy tissue is located at a position corresponding to the second area.

Additional Note 7

The processing circuitry may determine, when healthy tissue is located at a position corresponding to the second area, whether or not the tolerable dose of the healthy tissue is exceeded by irradiation of the radiation, and report information based on the determination result.

Additional Note 8

The processing circuitry may cause a display to display the acquired irradiation effect discrimination information superimposed on a medical image of a subject.

Additional Note 9

The processing circuitry may specify a penumbra area in the irradiation path as the second area and specify an area other than the penumbra area in the irradiation path as the first area.

Additional Note 10

The processing circuitry may specify the first area and the second area based on at least one of an irradiation depth of radiation in the irradiation path, radiation absorption characteristics of tissue in the irradiation area, and a penumbra in the irradiation area.

Additional Note 11

A radiotherapy planning method comprising:
acquiring dose rate distribution information indicating distribution of a dose rate in an irradiation path of radiation based on irradiation conditions of the radiation; and
acquiring irradiation effect discrimination information for discriminating irradiation effects of radiation in the irradiation path based on the acquired dose rate distribution information.

The invention claimed is:

1. A radiotherapy planning apparatus, comprising:
processing circuitry configured to:
acquire dose rate distribution information indicating a distribution of a dose rate in an irradiation path of radiation based on irradiation conditions of the radiation, the dose rate changing along an irradiation depth from a body surface; and
acquire irradiation effect discrimination information for discriminating irradiation effects of radiation in the irradiation path based on the acquired dose rate distribution information.

2. The radiotherapy planning apparatus according to claim 1, wherein the processing circuitry is further configured to acquire the dose rate distribution information based on the irradiation conditions of the radiation and information representing a relationship between the irradiation depth of the radiation and an attenuation rate of the radiation.

3. The radiotherapy planning apparatus according to claim 1, wherein the irradiation effect discrimination information acquired by the processing circuitry is information for discriminating irradiation effects of short-time, high-dose rate radiation.

4. The radiotherapy planning apparatus according to claim 1, wherein the processing circuitry is further configured to acquire the irradiation effect discrimination information based on a comparison between a dose rate indicated by the acquired dose rate distribution information and a predetermined threshold.

5. The radiotherapy planning apparatus according to claim 1, wherein the irradiation effect discrimination information acquired by the processing circuitry is information discriminating, in the irradiation path, between the first area in which the irradiation effects of the radiation can be attained and the second area in which the irradiation effects cannot be attained.

6. The radiotherapy planning apparatus according to claim 5, wherein the processing circuitry is further configured to prompt a change of the irradiation conditions when healthy tissue is located at a position corresponding to the second area.

7. The radiotherapy planning apparatus according to claim 5, wherein the processing circuitry is further configured to:
   determine, when healthy tissue is located at a position corresponding to the second area, whether or not a tolerable dose of the healthy tissue is exceeded by irradiation of the radiation; and
   report information based on the discrimination result.

8. The radiotherapy planning apparatus according to claim 5, wherein the processing circuitry is further configured to specify a penumbra area in the irradiation path as the second area and specify an area other than the penumbra area in the irradiation path as the first area.

9. The radiotherapy planning apparatus according to claim 5, wherein the processing circuitry is further configured to identify the first area and the second area based on at least one of the irradiation depth of radiation in the irradiation area, radiation absorption characteristics of tissue in the irradiation area, and a penumbra in the irradiation area.

10. The radiotherapy planning apparatus according to claim 1, wherein the processing circuitry is further configured to cause a display to display the acquired irradiation effect discrimination information superimposed on a medical image of a subject.

11. A radiotherapy planning method, comprising:
   acquiring dose rate distribution information indicating a distribution of a dose rate in an irradiation path of radiation based on irradiation conditions of the radiation, the dose rate changing along an irradiation depth from a body surface; and
   acquiring irradiation effect discrimination information for discriminating irradiation effects of radiation in the irradiation path based on the acquired dose rate distribution information.

* * * * *